(12) United States Patent
Graves et al.

(10) Patent No.: US 8,295,905 B2
(45) Date of Patent: Oct. 23, 2012

(54) MOVABLE INTEGRATED SCANNER FOR SURGICAL IMAGING APPLICATIONS

(75) Inventors: David Graves, Manitoba (CA); John Saunders, Manitoba (CA); Gord Klimenko, Manitoba (CA); Tony Lentz, Lockport (CA); Hong Yu, Manitoba (CA); Jonathan Li, Manitoba (CA); James Schellenberg, Manitoba (CA)

(73) Assignee: Imris Inc., Winnipeg, MB (CA)

( * ) Notice: Subject to any disclaimer, the term of this patent is extended or adjusted under 35 U.S.C. 154(b) by 384 days.

(21) Appl. No.: 11/765,845

(22) Filed: Jun. 20, 2007

(65) Prior Publication Data

US 2008/0039712 A1  Feb. 14, 2008

Related U.S. Application Data

(60) Provisional application No. 60/805,241, filed on Jun. 20, 2006.

(51) Int. Cl.
*A61B 5/05* (2006.01)

(52) U.S. Cl. ........ 600/411; 600/410; 600/409; 600/407; 324/318; 324/319; 324/322

(58) Field of Classification Search .................. 600/407, 600/410; 284/207
See application file for complete search history.

(56) References Cited

U.S. PATENT DOCUMENTS

| | | | |
|---|---|---|---|
| 4,939,464 A | 7/1990 | Hammer | |
| 5,239,259 A * | 8/1993 | Todoroki et al. | 324/114 |
| 5,300,910 A * | 4/1994 | Unkelbach et al. | 335/306 |
| 5,719,400 A | 2/1998 | Cherry | |
| 5,735,278 A | 4/1998 | Hoult et al. | |
| 5,842,987 A | 12/1998 | Sahadevan | |
| 5,998,792 A | 12/1999 | DiFilippo | |
| 6,023,165 A * | 2/2000 | Damadian et al. | 324/318 |
| 6,029,081 A * | 2/2000 | DeMeester et al. | 600/410 |
| 6,241,671 B1 * | 6/2001 | Ritter et al. | 600/427 |
| 6,242,919 B1 * | 6/2001 | Zuk et al. | 324/322 |
| 6,674,083 B2 | 1/2004 | Tanaka | |
| 6,782,571 B1 * | 8/2004 | Josephson et al. | 5/601 |
| 6,946,841 B2 | 9/2005 | Rubashov | |
| 7,286,867 B2 * | 10/2007 | Schlyer et al. | 600/407 |
| 2005/0033155 A1 | 2/2005 | Rezzonico et al. | |

* cited by examiner

*Primary Examiner* — Tse Chen
*Assistant Examiner* — Joel F Brutus
(74) *Attorney, Agent, or Firm* — Adrian D. Bathson; Ade & Company Inc.

(57) ABSTRACT

A patient imaging system includes a patient support table, an MRI system including a cylindrical magnet and a PET system including positron detectors mounted in a ring. The magnet defines a cylindrical bore for receiving the patient on the table where the magnet is mounted for rotation about a vertical axis on a slew ring carried on rails allowing longitudinal movement. The PET ring is mounted in the bore for longitudinal movement. The quench tube for the magnet passes through the slew ring with a rotary union at the axis. The shielding covers include a fixed upper part and a lower part which rotates about the axis with the magnet. The magnet is arranged in a two or three room diagnostic configuration in which a holding bay houses the magnet and the diagnostic patients are organized in the three rooms each cooperating with the magnet bay as the magnet is rotated.

21 Claims, 4 Drawing Sheets

MOVABLE INTEGRATED SCANNER FOR SURGICAL IMAGING APPLICATIONS

This application claims the benefit under 35 USC 119 of the filing date of Provisional Application 60/805241 filed Jun. 20, 2006.

This invention relates to a movable apparatus for obtaining medical scanned images of a patient. The apparatus may provide the possibility for combining and sequencing both PET and MRI detection capability for surgical imaging applications. The apparatus may provide movement in both translational and rotational directions to optimize the utility and effectiveness of the system.

BACKGROUND OF THE INVENTION

Both PET (Positron Emission Tomography) and MRI (Magnetic Resonance Imaging) are known techniques which can be used to image the body. In the case of PET, a solution is injected or taken into the body, the solution which contains molecules with positron emitting atoms. Therefore, once positron detector geometry is properly positioned around the patient, and once software is used to identify the location of the positron emission, the location and concentration of positron emitting molecules can be detected. One of the major molecules used is a derivative of glucose which can enter the cells as glucose but is not metabolised as glucose and so the regions of major activity in the body can be detected. If the molecules are specific for cancer then this imaging technique can be utilised to detect the location of the tumour. PET however does not provide any anatomical information, only information on the location of the positron emitting molecules. The PET images need to registered to the anatomy of the patient and this is where MRI can be very useful.

With MRI, a high field magnet, typically superconducting, is arranged in a torus configuration (like a donut) and with the patient lying down inside the magnet the magnetic field allows a pulsed and sequenced magnetic and EM field to probe the body to produce soft tissue images, which allow the trained radiologist to determine with high probability the anatomy of the patient. MRI is sometimes performed using contrast agents to provide even better contrast between different soft tissue types. MRI techniques are very good at detecting the anatomical location of many but not all tumours.

These two imaging techniques, MRI and PET, are orthogonal techniques, in that the PET detection technology can be constructed in such a way that it is unaffected by magnetic fields and the MRI system can be constructed to be unaffected by the PET techniques. For this reason, if an integrated PET and MRI detector system can be constructed, then the two systems can be operated in parallel or almost parallel manners in both space and time to allow for improved and more complete detection of tumour locations within the body.

PET and MRI can be used to obtain a functional image combined with anatomical image to provide the clinician with far more information than either technique alone. For example, positron emitting molecules can be developed which interact only with certain receptors in the brain and so these receptors can be observed by PET and then their actual location in the brain determined by the MRI.

PET imaging is also an established technique, with general knowledge being available as well as many patents on specific configurations of PET detectors.

U.S. Pat. No. 5,998,792 discusses a variable detector geometry in 1999, and describes PET imaging as follows:

In nuclear imaging, a radiopharmaceutical such as sup.99mTc or .sup.201 T1 is introduced into the body of a patient. As the radiopharmaceutical decays, gamma rays are generated. These gamma rays are detected and used to construct a clinically useful image.

Positron emission tomography (PET) is a branch of nuclear medicine in which a positron-emitting radiopharmaceutical such as .sup.18 F-Fluorodeoxyglucose (FDG) is introduced into the body of a patient. Each emitted positron reacts with an electron in what is known as an annihilation event, thereby generating a pair of 511 keV gamma rays. The gamma rays are emitted in directions approximately 180 degrees apart, i.e. in opposite directions.

A pair of detectors registers the position and energy of the respective gamma rays, thereby providing information as to the position of the annihilation event and hence the positron source. Because the gamma rays travel in opposite directions, the positron annihilation is said to have occurred along a line of coincidence connecting the detected gamma rays. A number of such events are collected and used to reconstruct a clinically useful image.

Various detector systems have been used in PET imaging. One class of PET systems can be termed non-rotating systems. The most common non-rotating systems have one or more rings of detector elements disposed in a circle about the patient. Other non-rotating systems include cylindrical shell detector systems and hexagonal multi-plate systems. In each of these systems, the detector surrounds or nearly completely surrounds the object to be scanned. Since coincidence events at substantially all transverse angles within a slice can be detected, system sensitivity is does not vary much between locations in a transverse slice.

Another class of PET systems can be termed rotating systems. Partial ring systems and dual or triple head gamma camera systems with coincidence detection capabilities fall into this category. One type of partial ring system includes two arcs of radiation sensitive detectors disposed on a generally circular rotating gantry. The arcs of radiation detectors are fixed with respect to each other so that their centers are generally diametrically opposed, with a slight angular offset. Rotating systems have partial transverse angle coverage such that it is necessary to rotate the detectors about the patient (or vice versa) in order to sample the transverse angles needed to reconstruct fully tomographic images. The sensitivity of these systems thus varies across the detector field of view. This variation in sensitivity is taken into account during processing of the coincidence data.

This description of the PET rotating and non-rotating geometries refers to the PET detector itself, and not to an integrated scanner using PET/MRI. U.S. Pat. No. 6,674,083 (Tanaka) issued Jan. 6, 2004 discusses a positron emission tomography apparatus.

The article "The New Challenges of Brain PET Imaging Technology", written in Current Medical Imaging Reviews, 2006, 2, 3-13, authored by Habib Zaidi and Marie-Louise Montandon, demonstrates through a prototype construction that combined PET/MRI scanners are possible. "Whole-Body Imaging with PET/MRI", European Journal of Medical Research, Jun. 30, 2004, page 309-312, states, regarding the combination of PET and MRI into a single scanner, "The combination of these two excellent diagnostic imaging modalities into a single scanner offers several advantages in comparison to PET and MRI alone".

"Simultaneous PET and NMR", The British Journal of Radiology, 75(2002),S53-S59 describes a small prototype PET scanner that is MR compatible is described. In this case, four meter sections of optical fiber are used to transport the scintillation signals to photomultiplier tubes that are removed from the high magnetic field area of the bore. They discuss the potential advantages for both temporal and spatial correlation. As they indicate in this paper, "incorporation of PET and MR scanners into a single gantry would keep subject motion and tissue deformation between PET and MR acquisitions to an absolute minimum, as is the approach adopted for the combined PET and CT systems described elsewhere in this special issue (their references 2, 3)"

Additional papers that include Simon Cherry as author are: "Simultaneous PET and MR imaging", Y. Shao et al, Phys. Med. Biol. October 1997 42(10), 1965-70; "Contemporaneous positron emission tomography and MR imaging at 1.5T", K. Farahani et al, J. Magn. Res. Imaging March 1999, 9(3): 497-500; "A study of artefacts in simultaneous PET and MR imaging using a prototype MR compatible PET scanner", RB Slates et al, Phys. Med. Biol. August 1999; 44(8):2015-27.

An additional publication is "MR-PET: Combining Function, Anatomy and More", M. Schwaiger et al, September 2005 Medical Solutions, pp. 25-30. This publication provides a simple diagram which shows a Magnetom Espree with a modified bore liner assembly. In this bore liner assembly is shown an RF body coil, above which is the PET camera elements. The diagram indicates that PET is acquired with a ring inserted into the magnet—simultaneous acquisitions are possible.

In U.S. Pat. No. 4,939,464 (Hammer) issued Jul. 3, 1990 is disclosed a combination NMR/PET scanner which uses light pipes to communicate the scintillation events to the exterior of the magnet. The PET scanner ring is mounted in the magnet bore and is moveable relative thereto.

In U.S. Pat. No. 6,946,841 (Rubashov) issued Sep. 20, 2005 is disclosed a combination NMR/PET scanner for breast tissue which where the PET scanner ring is mounted outside the magnet bore and the patient is moved between the two scanning positions.

In U.S. Pat. No. 5,719,400 (Cherry) issued Feb. 17, 1998 is disclosed a high resolution detector for use in PET scanning which is suitable for use in combined PET/MRI systems.

Further, previous publications and patents have shown it is possible to move a high-field superconducting MRI system in translation.

In U.S. Pat. No. 5,735,278 (Hoult et al) issued Apr. 7, 1998 is disclosed a medical procedure where a magnet is movable relative to a patient and relative to other components of the system. The moving magnet system allows intra-operative MRI imaging to occur more easily in neurosurgery patients, and has additional applications for liver, breast, spine and cardiac surgery patients. The system is used as follows:

The magnet is at first some distance from the operating table, either in the side or back of the surgical room or perhaps within a holding bay area;

When imaging is required, the MRI magnet is advanced from its holding area and positioned in the imaging position over the table;

Images are taken and magnet is retracted to its holding area. Thus the MRI system consists of:

Magnet;
Rails, installed on the site;
Magnet mover system, which consists of a magnet carriage, cable carrier, and mover control system.

SUMMARY OF THE INVENTION

According to a first aspect of the invention there is provided an for obtaining a scanned image of a part of a patient comprising:

a patient support table;

and a magnetic resonance imaging system for obtaining images of a part of the patient, the magnetic resonance imaging system comprising:

a magnet for use with a control system for controlling and varying the magnetic fields, a radio frequency transmission and detection system for eliciting and detecting from the part of the patient nuclear magnetic resonance signals, in response to the magnetic fields, including an RF probe arranged to be located adjacent to the part of the patient and a computer and display monitor for decoding and displaying the detected signals;

the magnet defining a cylindrical bore arranged such that the part of the patient is positioned in the bore so as to lie in the magnetic field of the magnet while the patient is located in place on the table;

the magnet being mounted for movement relative to the table horizontally in a direction longitudinal of the table, the mounting providing a first position of the magnet in which the part of the patient is positioned in the magnetic field of the magnet while the patient remains in place on the table;

and a positron emission tomography scanning system (PET) mounted on the magnet for use in conjunction with the magnetic resonance imaging system.

Preferably the PET system is movable.

Preferably the PET system is mounted on the magnet for common movement therewith.

Preferably the magnet is movable longitudinally along its axis.

Preferably the magnet is movable vertically.

Preferably the magnet is rotatable about a vertical axis through 180 degrees.

Preferably the PET system is mounted in the bore of the magnet for common movement therewith.

Preferably the PET system is mounted such that the field of view of the magnet coincides with the field of view of the PET.

Preferably the PET system is movable within the bore.

Preferably the PET system is mounted on the magnet at one end such that movement of the magnet carries the PET to a position aligned with the part of the patient.

Preferably the magnet is rotatable about a vertical axis to move the PET to a position adjacent the patient.

Preferably the PET includes optical fibers extending along the bore to carry optical signals from the scintillation detectors to an exterior control system.

Preferably the PET includes a wireless communication system to carry optical signals from the scintillation detectors to an exterior control system.

Preferably the magnet is mounted on a rail system and the PET system is mounted on same rail system for separate movement of the PET system relative to the magnet.

According to a second aspect of the invention there is provided an apparatus for obtaining a scanned image of a part of a patient comprising:

a patient support table;

and a magnetic resonance imaging system for obtaining images of a part of the patient, the magnetic resonance imaging system comprising:

a magnet for use with a control system for controlling and varying the magnetic fields, a radio frequency transmission and detection system for eliciting and detecting from the part of the patient nuclear magnetic resonance signals, in response to the magnetic fields, including an RF probe arranged to be located adjacent to the part of the patient and a computer and display monitor for decoding and displaying the detected signals;

the magnet defining a cylindrical bore arranged such that the part of the patient is positioned in the bore so as to lie in the magnetic field of the magnet while the patient is located in place on the table;

the magnet being mounted for rotation about a vertical axis.

Preferably the magnet is movable longitudinally along its axis.

Preferably the magnet is movable vertically.

Preferably the magnet is rotatable about a vertical axis through 180 degrees.

Preferably the magnet is rotatable about a vertical axis to move a front end of the magnet to a position adjacent the patient.

Preferably the magnet is movable on a support carried on rails in a longitudinal direction and wherein there is provided a turntable connecting the magnet to the support to allow the front face of the magnet to be turned to face in one or other direction along the rails.

The table may be a diagnostic table carried by the magnet which can be extended into a room where the patient lies on the diagnostic table and imaging is performed.

The table may be a surgical table which remains in place in the room for relative movement of the magnet which can be extended into a room where the patient lies on the surgical table and imaging is performed. The magnet may be arranged to carry a diagnostic table at one end and to co-operate with a surgical table at the other end.

The system is installed in renovated hospital buildings or in new buildings. The system can be installed in one-room or two-room configurations. In the two-room configuration, the magnet and MRI system is shared between the two rooms as needed by the hospital staff, leading to increased cost effectiveness within the business case.

Many room configurations can be discussed with this concept. Many applications can also be discussed, with the applications being limited by the size and extension of the operating room table and the limitations of the MRI scanner.

In some regions and countries there is a premium placed on patient safety which disallows the movement of the patient after surgery has started. Therefore, any design of the integrated PET/MRI scanner should move the scanner instead of moving the patient. This movement of the scanner could be in whole or in part, as long as the patient does not move. This same restriction on usage may eventually be true of interventional approaches, in that some interventional techniques require a significant number of penetrations of the body or aligned equipment items, which infer that patient movement should not be done.

Further, the MRI system has a magnetic field which is not equivalent in all directions with the magnetic field strength along the axis being different than in the two orthogonal directions. This means that the PET imaging portion of the system may be optimally sited on an off-axis orientation, which implies that rotation of the integrated scanner may be important.

The present arrangement moves the MRI in rotational and vertical directions as well to ensure that the integrated scanner is optimized.

The present arrangement assumes the presence of a scanner system that integrates both MRI and PET capability, and patents the movement of the integrated scanner in each of the six degrees of freedom of movement for the surgical, interventional and diagnostic imaging environments.

Additional unique multi-room layouts, configurations and applications are possible when a rotating MRI system is designed. In this case, the following multi-room configurations are used as examples to illustrate the variety of applications which are possible, with all of these applications being financially beneficial to the healthcare industry.

With these superconducting magnet systems, there are quench tubes, gradient cables, cooling cables of water and helium, and various control cables that need to be rotated as well. In addition, the rotation must be managed so that the rotation is 180 degrees in one direction and potentially 180 degrees in the other, if all 360 degrees of rotation is required.

The magnet system moves into a room within 1 minute, and the doors open within seconds, so the limiting factor on effectiveness of usage of the magnet system is providing the patients into and out of the room, prepping the patients if required, and discussing the imaging with the patients. It is known that a reasonable amount of time per imaging event is 60 minutes, and therefore the movement of the MRI scanner into and out of a room is not the limiting time value. As well, the efficiency of a multi-room system becomes more difficult to schedule as the need for both diagnostic and interventional procedures occurs. The following configurations are now possible:

A three room diagnostic configuration in which a central magnet holding bay houses the magnet and the diagnostic patients are organized in the three rooms. The doors to room one open, the magnet holding bay becomes part of room one, the magnet does not move but may extend its diagnostic table, the patient lies on the diagnostic table, imaging is performed, no need to do intervention is found, the patient exits the diagnostic table and the magnet moves back into the holding bay, ready for use by one of the other rooms. The magnet then may draw in its table, rotates to the doors for that room, and the process for the other room begins. In this case, the magnet does not move in a translational direction, such as on rails, but simply rotates.

A two room system which is in the corner of the hospital. In this case, the magnet both rotates and translates. There is a central magnet holding room, with doors in each of the two 90 degree directions, and the magnet can rotate its diagnostic table in whichever direction is required, or can rotate to allow the opposite end of the magnet to enter the room first. This approach allows existing diagnostic functionality and applications to be used in either room, or allows both rooms to serve as intra-operative rooms without any significant change to magnet controls and monitoring. This two room corner system cannot be done without a rotating magnet.

Similarly, any room configuration which is not of the in-line variety needs to have a rotating magnet.

In addition, in-line configurations can have increased flexibility as well if rotation is allowed. For example, one can join two diagnostic rooms with a magnet holding room in the middle. In this case, the MRI system rotates so that the diagnostic table is always the first entry into the room. This allows the diagnostic rooms to be as small as possible, allowing maximum density of the MRI system and the smallest cost in terms of square footage for the diagnostic room.

Many other room configurations can obviously be imagined for those skilled in the art of medical architecture and imaging systems.

If the MRI and PET methods are integrated together into a single device, one has an integrated scanner which uses orthogonal imaging technologies. Whereas previous work has assumed that the MR/PET scanner is stationary, a scanner which is capable of translational and rotational movement has unique attributes which are incorporated into this patent claim.

The following improvements arise:

PET Imaging can be done in one room, followed by MRI imaging in an adjacent room, based on the needs of the patient and surgical team, thus increasing the financial payback of the medical installation. In this case, there may be two different patients in these two rooms, and one patient needs PET imaging and one needs MRI.

More flexible PET and MR integration can be considered, in that when imaging a floppy gland during surgery no patient movement is required in order to perform imaging on multiple body sites.

If the PET imaging equipment is offset from the MRI field of view, simultaneous or near simultaneous imaging can provide information on more than one location within the body without moving the magnet.

If the PET imaging equipment is offset from the MRI field of view, the surgical team can image the same body part by first imaging using MRI capability and than move the magnet to achieve PET imaging capability of the same body part, thus allowing a flexibility of design for positioning the PET scintillators relative to the center of the field of view of the magnet.

If both PET and MRI detectors are designed as separate subsystems, but placed on the same rail system, it is possible to allow a given operating room to have independent PET and MRI detection applications at different times during the day.

If both PET and MRI detectors are available, and if the ceiling hung systems have the capability of being rotated, then the MRI and PET detectors can be used separately with a non-moving patient through the rotational and translational movement of the scanner system. In this case, the patient might be having an MRI scan, something is observed, after which the magnet is removed from the patient, the magnet is then rotated so that the PET system is pointed towards the patient, after which the PET system is moved over the patient, and the PET imaging is performed. There are some differences in the magnetic field of the MRI system for axial and non-axially oriented equipment elements which causes the rotational ability of the scanner system to be important.

If both PET and MRI detectors are available, and if the ceiling hung systems have the capability of being translated in both x and y coordinates, rotated and vertically lifted, then additional and different designs may be possible for the PET and MRI configurations.

With additional movement possibilities, the shimming effort required to provide the magnetic system with a homogenous environment is greatly reduced. Currently, the rebar in the floor makes a difference to the magnetic imaging system, unless it is stainless steel. If the MRI system can be moved in a multitude of manners, it is possible to find the optimum location within the room to provide imaging.

In addition, another complication of installing the ceiling hung system is that the table system moves with the floor but the ceiling system moves with the ceiling. If there is any sag in the ceiling that is not present in the floor, the systems move relative to each other, which changes the exact height distances. By allowing the magnet to move vertically, the same distance can be maintained between table and magnet. This approach is used instead of simply moving the table in those operations and circumstances where moving the patient even a little bit changes the imaging or affects the patient safety. For example, certain organs and glands, such as the prostate, may be so floppy or so degenerated that table motion is not allowed. In addition, when interventional work is being done, certain positions of the intervening tubes, needles or other apparatus is so sensitive that table motion is not recommended.

In addition, it is discussed to provide interventional capability within the system. Currently, there is technology called the Miyabi table from Siemens that provides docking onto the diagnostic table of Siemens. When the magnet can be rotated, this provides a new freedom of workflow for a room layout.

The advantages of the rotational system are not only for ceiling mounted systems. For floor-mounted systems, providing a rotating capability for the MRI allows the same advantages.

As well, it is possible to have relative movement between the PET and MRI systems. The PET system may be part of the bore system of the MRI, and can be moved relative to the field of view of the MRI. This movement relative to the MRI field of view may allow better or improved imaging performance.

Further, once one can rotate, translate or vertically move the integrated scanner, additional scanner designs become possible. In those cases where simultaneous scanning is desired, the PET focus area and the MRI field of view can be co-located through the design and configuration of the systems.

The integrated PET/MRI system can be suspended from the ceiling or mounted on a floor mounted bearing, with either system providing rotation of the magnet. The MRI system may also be suspended from the ceiling on rails, such that it can also be translated in space using the rail system. The rotational mechanism can either be located between the magnet and the rails, or above the rails. The below track and above track rotators have different properties for different configurations. The below track rotator allows for easiest upgrade of existing sites, whereas the above track rotator works like a roundhouse in a railway yard, in that the rail, MRI system and all associated systems are rotated.

DETAILED DESCRIPTION

Figure 1:
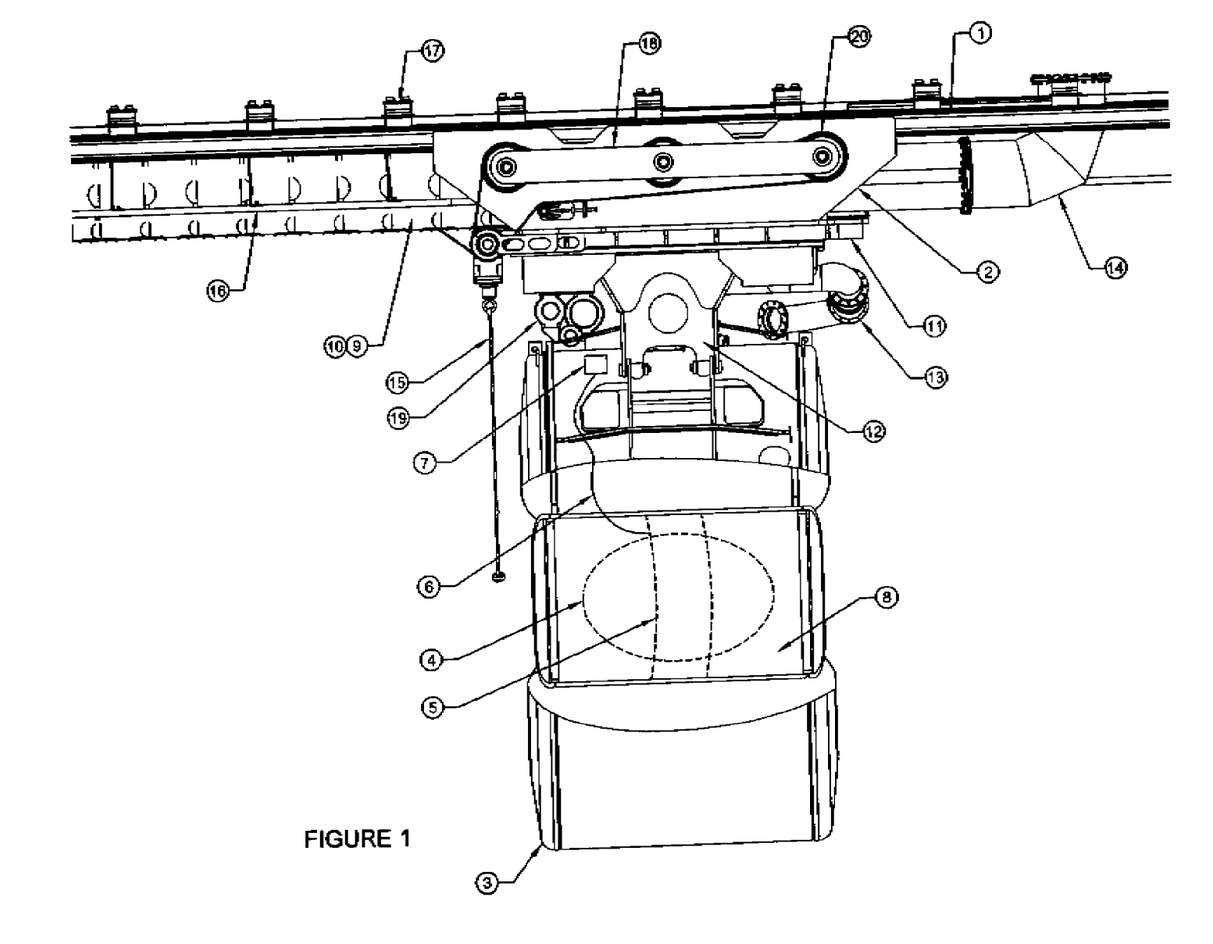
FIG. 1 is a side elevational view of an MRI magnet which includes the ability to allow rotation about a vertical axis and provides the addition of a PET detection system.

FIG. 1 shows the integrated PET/MRI scanner with rotating capacity. Ceiling rails 1 are bolted onto the structural steel of the building using Rail Clamps 17. Two ceiling rails are used, at a width apart approximately the same as the width of the magnet, although other widths are possible.

The magnet 3 is mounted onto the rails using a magnet Mover System 2. The upper part of the magnet Mover System traverses the rails, and does not rotate. The lower part of the magnet Mover System is connected to Slew Ring 11 so that it can rotate relative to the upper part. The Slew Ring 11 is motor driven, and carefully rotates the magnet system over a given angle, such as 90 degrees, 180 degrees or 270 degrees depending on the type of room layout being implemented. For both translational and rotational movements, the motor drive system can include gentle acceleration and deceleration in keeping with the requirements of the magnet system. The lower part of the magnet Mover System is bolted to the magnet using the Rotator to Magnet System 12.

For the rotational magnet system using the slew ring 11, it is necessary to allow rotation of the quench tube system so there is provided a fixed quench tube 14 mounted on the rails 1 and a rotational quench tube part 13 attached to the magnet. These quench tubes are joined together with a rotary union mounted at the iso-center of the magnet system, directly above the magnet and central of the slew ring, so that the rotation does not put undue stresses on the quench system. As it is difficult to ensure that the exact iso-center is achieved, it is practical to use a flex connection that absorbs some portion of the stresses that occur during rotation.

For a rotational MRI system it is also necessary to ensure that the cabling can be properly guided through the rotational arc. One method to do this uses a Cable Management System 19 that contains multiple tube guides, with different guides being used for communication cabling, power cabling, low voltage cabling, monitoring cabling and helium lines. The separation of these cables and the guidance of these cables through the rotational movement ensures that no binding and eventual breakage occurs. Again these components pass through the slew ring and connect to components carried on the rails with the movement of the magnet by a cable carrier system 9.

The magnet Mover System is moved via the belt drive translational system 18. This system uses wheels on top of the rail to carry the weight, and Drive Wheels 20 below the rail and contacted with the rail to allow movement to occur. Drive wheels and weight bearing wheels are placed on both of the rails, to ensure an even distribution of weight and a straight tracking performance for the system. A driveshaft may be used between the left and right belt drive translational systems to ensure that they move in harmony. In this case, a single motor may be used to drive both drive wheel sets. For safety, in the event of power outage, it is useful to have a Hand Crank 15 that allows the operators to remove the magnet from the patient if this movement is required. Operation of the hand crank requires the clutch to be disengaged in this particular design.

In addition to the translational movement provided by the rails and the rotational movement provided by the slew ring, vertical adjustment movement of the bore of the magnet is possible by adjustment of the height of the slew ring on the support 12.

The magnet has a round magnet bore 8 into which the table and patient can be positioned to allow imaging to occur. For a magnet such as the Siemens Espree (trade mark) magnet, the MRI Bore is 70 cm in diameter and approximately 125 cm in length. The magnet has a field of view 4 of 30 cm×45 cm×45 cm. The field of view is the volume within the system that allows high quality imaging to occur, and coincides with the volume over which the magnet field can be maintained within appropriate linearity. The patient's anatomy of interest is positioned within the field of view to allow imaging to occur.

A PET Detector Ring 5 is co-located with the magnet field of view, with each individual detector on the ring being connected via optical fiber in a bundle of fibers 6 to the multipliers 7 that are located above or around the magnet. The multipliers are shown on the top of the magnet, however they could be placed in alternative positions within the magnet. The optical fiber is wound in the cable carrier 9 which typically carries magnet and associated cables 10 that include quench tube, helium lines, water coolant lines, gradient cables, RF cables, control lines, and a variety of additional monitoring and sensing lines as required for various applications that are attached to the bore, cover-set, and other MRI elements. The cable carrier and associated cabling uses the cable carrier guides 16 to maintain the correct shape of the cables as they are moved with the system.

FIG. 1 shows an integrated PET/MRI scanner suitable for simultaneous scanning, because the PET imaging volume, which is inside the PET detector ring, overlaps the MRI field of view.

Alternate designs are also possible. For example, if the PET detector ring is moved to the end of the MRI bore, then the imaging volumes of the two imaging systems are not coincident, which would allow simultaneous imaging of two different body parts. Non-simultaneous scanning of the same body part in this scanner configuration must involve relative movement between the patient and the scanner. In general, this can be accomplished via one or a combination of three methods:

Move the integrated PET/MRI scanner and not the patient

Move the PET scanner inside the bore of the MRI without moving the patient.

Move the patient in some way. However it is preferable that the patient is never moved during scanning, and therefore methods 1 and 2 are preferred.

While FIG. 1 has shown a rotational PET/MRI scanner, it is possible to build a rotational MRI scanner for purely MRI scanning needs so that the same construction can be used with the PET scanner omitted.

Figure 2:
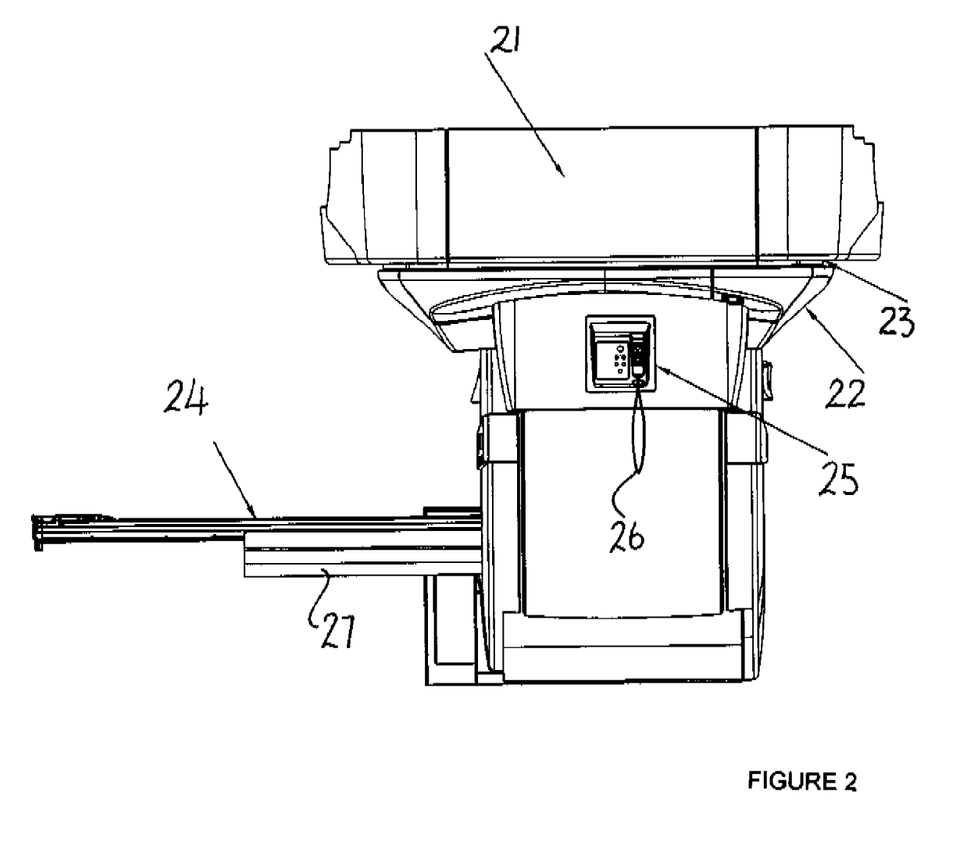
FIG. 2 is a side elevational view of the magnet of FIG. 1 showing further details of the covers and the diagnostic table which are omitted from FIG. 1 for convenience of illustration.
Figure 3:
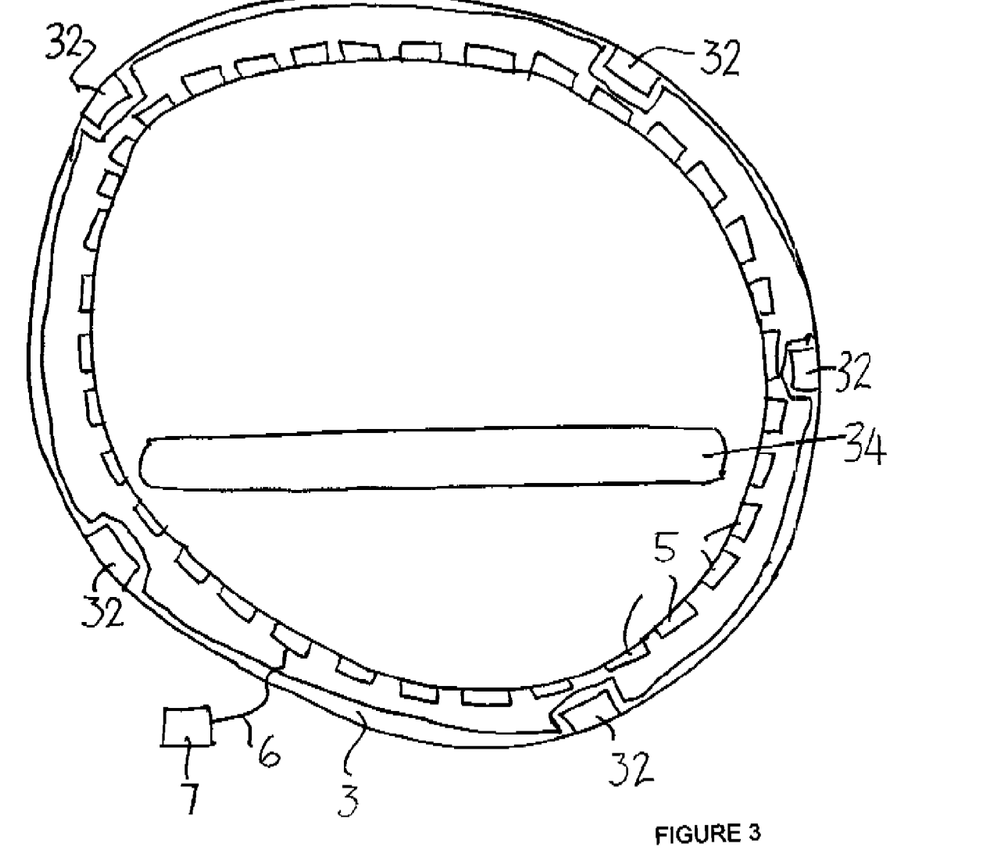
FIG. 3 is a cross-sectional view of the bore of the magnet of FIG. 1 showing the PET detector ring inside the bore.

FIG. 3 shows further details of the movable PET scanner suitable for simultaneous scanning, and is equivalent to the PET/MRI configuration of FIGS. 1 and 2. Thus the PET detector ring is mounted to move inside the bore. The magnet Bore 8 has five spacing and drive rails 32, onto which is fitted the pet detector ring 5. This pet detector ring is driven back and forth through the bore using the drive rails 32, but the diagnostic or operating table 34 is sized such that no collision occurs as these elements are being moved inside the bore. The PET detector ring 5 has on its inside circumference a multitude of individual PET detectors 55 which generate their output, typically through scintillation, with this output being passed into optical fibers 6 which allow transmission from the scintillator detectors to the multipliers 7.

Two variations on the placement method of the optical fiber are possible where either the optical fiber goes through the sidewall of the bore, and so this method is only appropriate for the case where the PET detector ring does not move inside the bore, or the optical fiber does not go directly through the bore but instead is led to the end of the bore, where an optical fiber management system can accommodate the slack. In this design, the patient enters only from the opposite end of the bore 8, because the other end is used for optical fiber management. Alternatively, more sophisticated optical fiber management can be provided to allow both ends of the PET/MRI integrated scanner to be used.

An alternative design to those above can use wireless transmission of optical signals, with the bore having clear areas within its design which allows for light to pass through. In this arrangement, the PET detector ring generates EM wavelength suitable for optical fiber to transmit directly into the optical fiber and on to the multiplier.

Alternatively a system can be provided in which the PET scanner and magnet field of view are fixed in position relative to each other, with the entire integrated scanner moving instead. In this case, the integrated scanner moves on the ceiling rails, and rotates or moves vertically, in the manner that has already been discussed.

FIG. 2 shows a rotational MRI shielding cover-set. Conventional designs for such covers for magnets used in MRI are well known by persons skilled in the art. This cover-set is designed with an upper portion 21 which does not rotate and a lower portion 22 which does rotate, with the two portions being separated at a rotational seam 23.

FIG. 2 also shows a configuration which uses a diagnostic table 24 extending from the left side of the magnet. For the specific case of the Siemens Espree (trademark) magnet, the diagnostic table is attached to the magnet and can move in and out of the magnet for diagnostic imaging. The figure also shows the control panel 25 for the system. In this case, there is a set of controls installed on the magnet which includes a pendant control 26 connected to the magnet by a cable.

Figure 4:
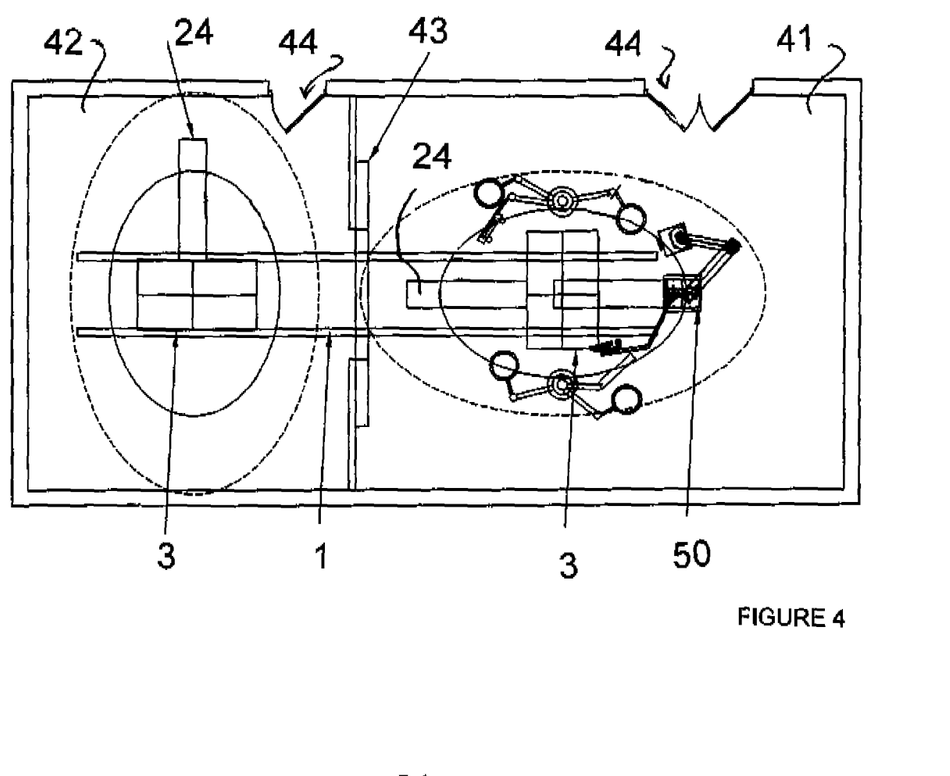
FIG. 4 is a schematic plan view of the magnet system of FIG. 1 mounted in a two room configuration.

FIG. 4 shows a floor layout in which the translating, rotating and vertically moving scanner is used in a two room configuration to service both an adult and a child. FIG. 7a shows a two room layout in which first room 41 is separated from second room 42 via sliding doors 23, with patients and medical team accessing the rooms via patient entry doors 44. The integrated scanner can move between these two rooms.

FIG. 4 shows two positions for this integrated scanner. The rails 1 allow the scanner to move between the rooms. The scanner position in room 41 is shown as it moves towards the surgical imaging position, in which the scanner 3 moves over the table 50 and in which the Siemens diagnostic table 24 is attached to the rear of the scanner as is the custom with the Siemens Espree (trademark), for example. This same scanner, when required, can be moved to a second position in room 42 in which the scanner 3 is rotated to allow the diagnostic table 24 to be positioned for interventional work. This rotation increases the utility of the system by minimizing the amount of space and access required in the second room 42.

The movement of the imaging system between the two rooms will increase the complexity of the shimming requirements of the MRI system, that is the difficulty of providing shielding for the signals and magnetic field required for the MRI experiments. Also, even if the particular locations within the various rooms are difficult to shim for MRI usage, those locations can be still be used for PET imaging, leading to an increased utility of the system in various room configurations.

Figure 5:
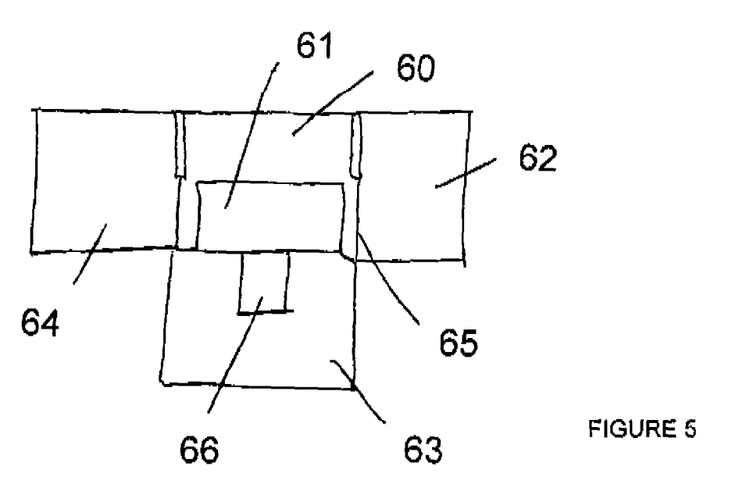
FIG. 5 is a schematic plan view of the magnet system of FIG. 1 mounted in a three room configuration.

FIG. 5 shows a three room diagnostic configuration in which a central magnet holding bay 60 houses the magnet 61 and the diagnostic patients are organized in the three rooms 62, 63 and 64. The doors 65 to one of the rooms 62, as selected from the three rooms, can be opened for example by retraction to one side so that the magnet holding bay becomes part of that room 62, the magnet does not move but may extend its diagnostic table 66, the patient lies on the diagnostic table, imaging is performed, no need to do intervention is found, the patient exits the diagnostic table and the magnet moves back into the holding bay, ready for use by one of the other rooms. The magnet then may draw in its table 66, rotates to the doors for that room, and the process for the other room begins. In this case, the magnet does not move in a translational direction, such as on rails, but simply rotates.

The front face can carry a PET scanning system so that the PET can be moved into position if required. If there is no PET system used, the front face may be arranged so that the magnet is not symmetrical and requires that the front face be moved into the position of the patient.

In an alternative arrangement, the magnet is mounted on a rail system along which can roll a support and on which is carried the slew ring allowing the magnet to rotate about its vertical axis. In this way the front face of the magnet can be moved to face the room. In this embodiment the patient table is located in the respective room so that the magnet moves to and relative to the table.

In addition, in-line configurations can have increased flexibility as well if rotation is allowed. For example, one can join two diagnostic rooms with a magnet holding room in the middle. In this case, the MRI system rotates so that the diagnostic table is always the first entry into the room. This allows the diagnostic rooms to be as small as possible, allowing maximum density of the MRI system and the smallest cost in terms of square footage for the diagnostic room.

There are advantages to simply hanging the MRI magnet from the ceiling. It is possible that vibration effects are reduced when the magnet is suspended, instead of floor mounted, leading to reduced vibrations and improved signal to noise performance.

It will be appreciated that the magnet may be arranged to carry a diagnostic table at one end such that on entry into a diagnostic room or on rotation of the magnet to co-operate with that diagnostic room, the table is made available for patients in that room. The magnet in a surgical situation is arranged to co-operate with a table present in the room which remains in the room when the magnet is moved so as to allow surgery to continue. In a hybrid situation, the magnet may carry the table at one end and be arranged to co-operate with a surgical table at the other end, thus requiring rotation of the table about its vertical axis.

Need for wall shielding, because when the magnet is rotated the field can go through the other side of the wall, impinging on hallways or other areas. The methods that can be used to limit this effect include: standard techniques that use additional metal in the walls to provide shielding, use of active coils embedded in the walls that turn on only when the rotational action occurs, power cycling of the MRI active coils, in which the active coils on the magnet either are increased or decreased in current so that the field does not extend so far.

Quench tube design, in which the quench tube must be designed to go through the iso-center of the rotating mass Cable routing design, in which the cabling is designed to be rotated 180 degrees. One method of doing the cable routing is to pre-route the cabling 90 degrees, and then the maximum cable bending is +/−90 degrees to achieve the full 180 degrees rotation. In this case, the cables are usually at the 90 degrees bend radius during their lifetime. Alternatively, one can design a rotation plate that allows 180 degree rotational couplings to couple the cable on the magnet to the cable extending back to the fixed wall mount location.

The arrangement described herein provides the following features and advantages:

The use of the circular slew ring so that the magnet effects of the ring are homogenous during rotation, which allows for the minimum effect on the shimming software of the magnet.

For the Espree magnet, it is useful to pull in the diagnostic table prior to rotation, to allow for a minimum radius of rotation, a minimum strain on the rotating motor, and a maximum for operator safety. If the diagnostic table would extend further out of the magnet, it would increase the probability of collision between the operator and the rotating system, or the collision between the rotating system and equipment items inside the room.

To allow rotation, the cover-set of the magnet, along with the brackets that holds the cover-set onto the magnet provide an upper part of the cover-set which does not rotate and a lower part of the cover-set that does rotate with the magnet.

To optimize the rotational performance, there is provided a motor system that gently accelerates and decelerates in a programmed and programmable way. If the start and stop forces that are exerted on the magnet are excessive, vibration can be caused and potentially shorter life can occur.

To optimize the safety of the rotating system, the control system includes "lock-outs" that will not allow the rotation to occur unless the proper orientation, location, door condition or other specific conditions are met by the environment. This lock-out capability ensures that the magnet cannot be rotated if the environment is not ready to receive the rotation.

The invention claimed is:

1. A method for imaging a part of a patient comprising:
providing a plurality of rooms each arranged for use in imaging a patent from said plurality of patients independently, the plurality of rooms including at least a first room and a second room;
providing a first patient support table arranged for interventional procedures on a first patient and mounted in the first room;
providing a magnetic resonance imaging system for obtaining images of a part of a patient from the plurality of patients, the magnetic resonance imaging system comprising:
  a magnet having a cylindrical bore with a horizontal axis of the bore longitudinal of the magnet;
  a control system for controlling and varying magnetic fields of the magnet,
  a radio frequency transmission and detection system for eliciting and detecting NMR signals from the part in response to the magnetic fields,
  an RF probe arranged to be located adjacent to the part at an imaging location in the bore; and
  a computer and display monitor for decoding and displaying the detected signals;
  and a diagnostic table carried at a first end of the bore for movement relative to the magnet longitudinally of the bore toward a second end of the bore for carrying the part into an imaging location in the bore;
the magnet surrounding the cylindrical bore with the horizontal axis of the bore longitudinal of the magnet arranged such that the part of the patient is positioned in the bore so as to lie in the magnetic field of the magnet while the patient is located in place on the table;
moving the magnet and its bore from the second room to the first room along a longitudinally extending support in a longitudinal direction along the horizontal axis of the bore so as to move the magnet and its bore into a position surrounding the first table for locating the part of the first patient on the first table at the imaging location;
moving the diagnostic table carried on the magnet on the longitudinally extending support from the second room to the first room;
in the second room, imaging a second patient from said plurality of patients by placing the patient on the diagnostic table in the second room magnet;
during said moving of the magnet from the second room to the first room rotating the magnet and its bore together with the diagnostic table carried thereon about a vertical axis passing through the bore relative to the longitudinally extending support so as to rotate the magnet and the horizontal bore axis about the vertical axis;
the rotating of the magnet and its bore being arranged such that the second end of the bore is presented to the first table and the first end of the bore is spaced away from the first table so that the magnet and its bore is moved into the position surrounding the first table for locating the part of the first patient on the first table at the imaging location;
and in the first room imaging the first patient using the magnetic resonance imaging system with the first patient located on the first table.

2. A method for imaging a part of a plurality of patients comprising:
providing a plurality of rooms each arranged for use in imaging a patient from said plurality of patients independently, the plurality of the rooms including at least a first room and a second room;
providing a magnetic resonance imaging system for obtaining images of a part of a patient of the plurality of patients, the magnetic resonance imaging system comprising:
  a magnet having a cylindrical bore with a horizontal axis of the bore longitudinal of the magnet;
  a control system for controlling and varying magnetic fields of the magnet,
  a radio frequency transmission and detection system for eliciting and detecting NMR signals from the part in response to the magnetic fields,
  an RF probe arranged to be located adjacent to the part at an imaging location in the bore,
  a computer and display monitor for decoding and displaying the detected signals;
  and a diagnostic table carried at a first end of the bore for movement relative to the magnet longitudinally of the bore toward a second end of the bore for carrying the part into an imaging location in the bore;
providing a first patient support table mounted in the first room arranged for interventional procedures on a first patient from said plurality of patients;
in the second room imaging a second patient of the plurality of patients using the magnetic resonance imaging system with the second patient located on the diagnostic table;
moving the magnet from the second room to the first room by;
  rotating the magnet and its bore about a vertical axis passing through the bore relative to the longitudinally extending support; and
  moving the magnet and its bore in a longitudinal direction along the horizontal axis of the bore from the second room into the first room;
the rotating of the magnet and its bore being arranged such that the second end of the bore is presented to the first table and the first end of the bore is spaced away from the first table so that the magnet and its bore is moved into a position surrounding the first table for locating the part of the first patient on the first table at the imaging location;
and in the first room imaging the first patient using the magnetic resonance imaging system with the first patient located on the first table.

3. The apparatus according to claim 2 wherein the magnet is rotatable about the vertical axis through an angle of at least 180 degrees.

4. The apparatus according to claim 2 wherein magnet is rotated on a circular slew ring so that the magnet effects of the ring are homogenous during rotation.

5. The apparatus according to claim 2 including covering the magnet with a shielding cover-set and causing an upper part of the cover-set to remain stationary as the magnet rotates and a lower part of the cover-set to rotate with the magnet.

6. The apparatus according to claim 2 including providing a quench tube for discharging a cooling liquid in the event that the liquid gasifies, and causing a stationary portion of the quench tube to remain stationary as the magnet rotates and a rotary portion to rotate with the magnet and providing a rotary union between the portions located on the vertical axis of rotation of the magnet.

7. A method for imaging a part of a plurality of patients comprising:
provideing a plurality of rooms each arranged for use in imaging a patient from said plurality of patients independently, the plurality of the rooms including at least a first room and a second room;
providing a magnetic resonance imaging system for obtaining images of a part of a patient of the plurality of patients, the magnetic resonance imaging system comprising:
a magnet having a cylindrical bore with a horizontal axis of the bore longitudinal of the magnet;
a control system for controlling and varying magnetic fields of the magnet,
a radio frequency transmission and detection system for eliciting and detecting NMR signals from the part in response to the magnetic fields,
an RF probe arranged to be located adjacent to the part at an imaging location in the bore,
a computer and display monitor for decoding and displaying the detected signals;
and a diagnostic table at a first end of the bore for movement relative to the magnet longitudinally of the bore toward a second end of the bore for carrying the part into an imaging location in the bore;
providing a first patient support table mounted in the first room arranged for interventional procedures on a first patient from said plurality of patients;
in the second room imaging a second patient of the plurality of patients using the magnetic resonance imaging system with the second patient located on the diagnostic table;
moving the magnet from the second room to the first room by;
rotating the magnet and its bore about a vertical axis passing through the bore relative to the longitudinally extending support; and
moving the magnet and its bore in a longitudinal direction along the horizontal axis of the bore from the second room into the first room;
in the first room the magnet and its bore being moved into a position surrounding the first table for locating the part of the first patient on the first table at the imaging location;
and in the first room imaging the first patient using the magnetic resonance imaging system with the first patient located on the first table.

8. The apparatus according to claim 7 wherein the magnet is rotatable about the vertical axis through an angle of at least 180 degrees.

9. The apparatus according to claim 7 wherein magnet is rotated on a circular slew ring so that the magnet effects of the ring are homogenous during rotation.

10. The apparatus according to claim 7 including covering the magnet with a shielding cover-set and causing an upper part of the cover-set to remain stationary as the magnet rotates and a lower part of the cover-set to rotate with the magnet.

11. The apparatus according to claim 7 including providing a quench tube for discharging a cooling liquid in the event that the liquid gasifies, and causing a stationary portion of the quench tube to remain stationary as the magnet rotates and a rotary portion to rotate with the magnet and providing a rotary union between the portions located on the vertical axis of rotation of the magnet.

12. A method for imaging a part of a plurality of patients comprising:
providing a plurality of rooms each arranged for use in imaging a patient from said plurality of patients independently, the plurality of the rooms including at least a first room and a second room;
providing a magnetic resonance imaging system for obtaining images of a part of a patient of the plurality of patients, the magnetic resonance imaging system comprising:
a magnet having a cylindrical bore with a horizontal axis of the bore longitudinal of the magnet;
a control system for controlling and varying magnetic fields of the magnet,
a radio frequency transmission and detection system for eliciting and detecting NMR signals from the part in response to the magnetic fields,
an RF probe arranged to be located adjacent to the part at an imaging location in the bore,
a computer and display monitor for decoding and displaying the detected signals;
providing a first patient support table mounted in the first room arranged for interventional procedures on a first patient from said plurality of patients;
in the second room imaging a second patient of the plurality of patients using the magnetic resonance imaging system with the second patient located on the diagnostic table;
moving the magnet from the second room to the first room by;
rotating the magnet and its bore about a vertical axis passing through the bore relative to the longitudinally extending support; and
moving the magnet and its bore in a longitudinal direction along the horizontal axis of the bore from the second room into the first room;
in the first room the magnet and its bore being moved into a position surrounding the first table for locating the part of the first patient on the first table at the imaging location;
and in the first room imaging the first patient using the magnetic resonance imaging system with the first patient located on the first table.

13. The apparatus according to claim 12 wherein the magnet is rotatable about the vertical axis through an angle of at least 180 degrees.

14. The apparatus according to claim 12 wherein magnet is rotated on a circular slew ring so that the magnet effects of the ring are homogenous during rotation.

15. The apparatus according to claim 12 including covering the magnet with a shielding cover-set and causing an upper part of the cover-set to remain stationary as the magnet rotates and a lower part of the cover-set to rotate with the magnet.

16. The apparatus according to claim 12 including providing a quench tube for discharging a cooling liquid in the event that the liquid gasifies, and causing a stationary portion of the quench tube to remain stationary as the magnet rotates and a rotary portion to rotate with the magnet and providing a rotary union between the portions located on the vertical axis of rotation of the magnet.

17. A method for imaging a part of a plurality of patients comprising:
providing a plurality of rooms each arranged for use in imaging a patient from said plurality of patients independently, the plurality of the rooms being arranged such that each abuts a central area between the rooms;

providing a magnetic resonance imaging system for obtaining images of a part of a patient of the plurality of patients, the magnetic resonance imaging system comprising:
  a magnet having a cylindrical bore with a horizontal axis of the bore longitudinal of the magnet;
  a control system for controlling and varying magnetic fields of the magnet,
  a radio frequency transmission and detection system for eliciting and detecting NMR signals from the part in response to the magnetic fields,
  an RF probe arranged to be located adjacent to the part at an imaging location in the bore,
  a computer and display monitor for decoding and displaying the detected signals;
  and a diagnostic table at a first end of the bore for movement relative to the magnet longitudinally of the bore toward a second end of the bore for carrying the part into an imaging location in the bore;
locating the magnet in the central area between the rooms;
without moving the magnet laterally, rotating the magnet and its bore about a vertical axis passing through the bore relative to the longitudinally extending support;
  the rotating of the magnet causing the diagnostic table to be rotated around the axis so as to move the diagnostic table to each of the rooms in turn;
  and in each of the rooms imaging the first patient using the magnetic resonance imaging system with the patient located on the diagnostic table.

18. The apparatus according to claim 17 wherein the magnet is rotatable about the vertical axis through an angle of at least 180 degrees.

19. The apparatus according to claim 17 wherein magnet is rotated on a circular slew ring so that the magnet effects of the ring are homogenous during rotation.

20. The apparatus according to claim 17 including covering the magnet with a shielding cover-set and causing an upper part of the cover-set to remain stationary as the magnet rotates and a lower part of the cover-set to rotate with the magnet.

21. The apparatus according to claim 17 including providing a quench tube for discharging a cooling liquid in the event that the liquid gasifies, and causing a stationary portion of the quench tube to remain stationary as the magnet rotates and a rotary portion to rotate with the magnet and providing a rotary union between the portions located on the vertical axis of rotation of the magnet.

* * * * *